United States Patent
Lawrence et al.

(10) Patent No.: US 11,564,405 B2
(45) Date of Patent: Jan. 31, 2023

(54) REDUCING THE RISK OF VIRAL INFECTION DUE TO VIRAL CONTAMINATED FEED

(71) Applicant: Novus International, Inc., St. Charles, MO (US)

(72) Inventors: Bradley Van Lawrence, St. Charles, MO (US); Robert Edward Buresh, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 144 days.

(21) Appl. No.: 16/807,970

(22) Filed: Mar. 3, 2020

(65) Prior Publication Data
US 2020/0281227 A1 Sep. 10, 2020

Related U.S. Application Data

(60) Provisional application No. 62/813,247, filed on Mar. 4, 2019.

(51) Int. Cl.
*A23K 20/105* (2016.01)
*A61K 31/192* (2006.01)
*A61P 31/12* (2006.01)
*A23K 50/30* (2016.01)

(52) U.S. Cl.
CPC ............ *A23K 20/105* (2016.05); *A23K 50/30* (2016.05); *A61K 31/192* (2013.01); *A61P 31/12* (2018.01)

(58) Field of Classification Search
CPC ............................ A61K 31/192; A61K 31/194
USPC .................................................. 514/568, 574
See application file for complete search history.

(56) References Cited

U.S. PATENT DOCUMENTS

| | | |
|---|---|---|
| 2010/0098802 A1 | 4/2010 | Navarro |
| 2017/0354167 A1 | 12/2017 | Jones et al. |
| 2018/0207260 A1 | 7/2018 | Hernandez et al. |

FOREIGN PATENT DOCUMENTS

| | | | |
|---|---|---|---|
| CN | 105639124 A | | 6/2016 |
| CN | 107712313 A | * | 2/2018 |
| WO | 2020/180877 A1 | | 9/2020 |

OTHER PUBLICATIONS

ACTIVATE® DA, NOVUS Data Sheet, 2013, https://na98.salesforce.eom/sfc/p/#E0000000Xz5h/a/E0000000Xblw/f6DIHfQqXHr2iue15HSQPaDyH_TgL72W31NQqlliR4k (Year: 2013).*
Cottingim et al., Feed additives decrease survival of delta coronavirus in nursery pig diets, Porcine Health Management, 2017, 3:5 DOI 10.1186/s40813-016-0048-8, 7 pages.
Cottingim, Management and feeding strategies to reduce the impact of porcine delta coronavirus in nursery pigs, M.S. Thesis, May 2018, University of Minnesota, 128 pages.
Cottingim et al., Effect of additive on the survival of porcine delta coronavirus and porcine epidemic diarrhea virus in swine feed, 2015 Allen D. Leman Swine Conference, College of Veterinary Medicine, University of Minnesota, Recent Research Reports, 2015, vol. 42, p. 11.
Dee et al., An evaluation of contaminated complete feed as a vehicle for porcine epidemic diarrhea virus infection of naïve pigs following consumption via natural feeding behavior: proof of concept, BMC Veterinary Research 2014, 10:176 http://www.biomedcentral.com/1746-6148/10/176, 9 pages.
Dee et al., Modeling the transboundary risk of feed ingredients contaminated with porcine epidemic diarrhea virus, BMC Veterinary Research, 2016, 12:51 DOI 10.1186/s12917-016-0674-z, 12 pages.
Dee et al., Survival of viral pathogens in animal feed ingredient under transboundary shipping models, PLoS ONE, 2018, 13(3): e0194509, 18 pages.
Joshi et al., Pathogenesis of senecavirus A infection in finishing pigs. J. Gen Viol, 2016, 97:3267-3279.
Joshi et al., Detection of the emerging piconavirus senecavirus A in pigs, mice, and houseflies, J Clin Microbiol, 2016, 54:1536-1545.
Trudeau et al., Survival and mitigation strategies of porcine epidemic diarrhea virus (PEDV) in complete feed, American Dairy Science Association, Midwest American Society of Animal Science Meeting, 2015, Abstract 408, 2 pages.
Trudeau et al., Comparison of thermal and non-thermal processing of swine feed and the use of selected feed additive on inactivation of porcine epidemic diarrhea virus (PEDV), PLoS ONE, 2016, 11(6): e0158128 doi:10.1371j/ournal.pone.0158128, 13 pages.
International Search Report and Written Opinion for PCT/US2020/020813 dated May 19, 2020, 10 pages.
ACTIVATE® DA Product Label, Novus International, Inc.
ACTIVATE® DA Safety Data Sheet, Novus International, Inc., revised Jul. 25, 2019, 7 pages.

* cited by examiner

*Primary Examiner* — Shengjun Wang
(74) *Attorney, Agent, or Firm* — Polsinelli PC

(57) ABSTRACT

Methods for reducing the risk of viral infection in animals due to consumption of viral contaminated feed. The methods comprise administering to an animal in need thereof an effective amount of a feed additive, wherein the feed additive comprises a mixture of organic acids. The methods can be used to reduce the risk of infection in animals whose feed may or may not be contaminated with certain viruses.

10 Claims, No Drawings

REDUCING THE RISK OF VIRAL INFECTION DUE TO VIRAL CONTAMINATED FEED

CROSS-REFERENCE TO RELATED APPLICATIONS

This application claims the benefit of U.S. Provisional Application No. 62/813,247, filed Mar. 4, 2019, which is hereby incorporated by reference in its entirety.

FIELD

The present disclosure is directed to means for reducing the risk of viral infection in animals due to consumption of viral contaminated feed.

BACKGROUND

It is believed that porcine epidemic diarrhea virus (PEDV) was introduced into the United States in 2013 via contaminated feed ingredient container which allowed introduction of the virus into animal feed. It has been demonstrated that viral pathogens are able to survive in animal feed ingredients or feed products during transboundary shipping (Dee et al., PLOS ONE 13(3): e0194509.) Evidence suggests that certain feed additives may decrease viral survival and viral load in feed contaminated with some viruses (Cottingim et al, 2015, Allen D. Leman Swine Conference; Cottingim et al, 2017, Porcine Health Management 3:5 DOI 10.1186/s40813-016-0048-8). What is needed, therefore, are means for reducing the risk of infection in animals due to consumption of feed that may be contaminated with viruses.

SUMMARY

One aspect of the present disclosure encompasses a method for reducing risk of infection due to consumption of feed contaminated with a virus, the method comprising administering to an animal in need thereof an effective concentration of a feed additive, wherein the feed additive comprises a mixture of organic acids, and the virus is porcine epidemic diarrhea virus (PEDV), porcine reproductive and respiratory syndrome virus (PRRSV), or Seneca Valley A virus (SVA).

Another aspect of the present disclosure provides a method for reducing risk of infection by a virus in an animal, the method comprising administering to the animal an effective amount of a feed additive, wherein the feed additive comprises a mixture of organic acids, the animal's feed is or is not contaminated with the virus, and the virus is porcine epidemic diarrhea virus (PEDV), porcine reproductive and respiratory syndrome virus (PRRSV), or Seneca Valley A virus (SVA).

Other aspects and iterations of the present disclosure are discussed in more detail below.

DETAILED DESCRIPTION

The present disclosure provides methods for reducing or mitigating the risk of viral infection in animals due to consumption of feed contaminated with a virus. The methods comprise administering to an animal in need thereof an effective amount of a feed additive, wherein the feed additive comprises a mixture of organic acids. The methods disclosed herein may also be used reduce the risk of viral infections in animals whose feed may or may not be contaminated with certain viruses.

(I) Method for Reducing the Risk of Infection Due to Consumption of Viral Contaminated Animal Feed One aspect of the present disclosure provides methods for reducing or mitigating the risk of infection in animals due to consumption of feed contaminated with a virus. In particular, the method comprises administering to an animal in need thereof an effective concentration of a feed additive comprising a mixture of organic acids, which generally includes 2-hydroxy(methylthio)butanoic acid (HMTBA).

(a) Contaminated Feed

The animal feed may be contaminated with a variety of viral pathogens. Examples of possible viruses include porcine epidemic diarrhea virus (PEDV), porcine reproductive and respiratory syndrome virus (PRRSV), Seneca Valley A virus (SVA), foot and mouth disease virus (FMDV), classical swine fever virus (CSFV), African swine fever virus (ASFV), influenza A virus of swine (IAV-S), pseudorabies virus (PRV), Nipah virus (NiV), swine vesicular disease virus (SVDV), vesicular stomatitis virus (VSV), porcine circovirus type 2 (PCV2), vesicular exanthema of swine virus (VESV), porcine delta coronavirus (PDCoV), transmissible gastroenteritis virus (TGEV), porcine sapelovirus (PSV), bovine viral diarrhea virus (BVDV), bovine herpesvirus type 1 (BHV-1), bovine respiratory syncytial virus (BRSV), bovine parainfluenza type 3, canine distemper virus (CDV), feline calicivirus (FCV), chicken anemic virus (CAV), avian pox virus (APV), Newcastle disease virus (NDV), avian infection bronchitis virus (AIBV), avian influenza A virus (AIV), highly pathogenic avian influenza virus (HPAIV), and the like. In some embodiments, the feed may be contaminated with PEDV, PRRSV, or SVA. In specific embodiments, the feed may be contaminated with PEDV.

The feed may be contaminated by the inclusion of virally contaminated feed ingredients. Non-limiting examples of feed ingredients that may be contaminated with viruses include amino acids (e.g., lysine, methionine, leucine, valine, and the like), vitamins (vitamin D, vitamin C, and so forth), minerals (e.g., calcium, magnesium, zinc, copper, and the like), other nutrients (e.g., phosphorous, choline, betaine, etc.), enzymes (e.g., phytases, xylanases, proteases, and the like), probiotics (e.g., *Lactobacillus, Bacillus, Streptococcus, Pediococcus, Enterococcus, Bifidobacterium*, or combinations thereof), prebiotics (e.g., lactulose, mannan-oligosaccharide, inulin, fructo-oligosaccharide, galacto-oligosaccharide, and the like), oils or fats (e.g., vegetable oils, oilseed oils, rendered animal fats, and so forth), protein meals (e.g., soybean meal, corn meal, corn gluten meal, fish meal, blood meal, etc.), protein cakes (e.g., soybean cake, soybean oil cake, and so forth), feed pellets, milled grains, brewer's grains, and so forth. Alternatively, the feed may be contaminated with virus from some other source.

(b) Feed Additive

The feed additive used in the methods disclosed herein comprises a mixture of organic acids. In general, the feed additive comprises two or more organic acids. In some embodiments, the feed additive may comprise two organic acids. In other embodiments, the feed additive may comprise three organic acids. In still other embodiments, the feed additive may comprise four organic acids. In further embodiments, the feed additive may comprise five organic acids. In additional embodiments, the feed additive may comprise more than five organic acids.

The organic acids may be carboxylic acids or hydroxy acids (i.e., carboxylic acids substituted with hydroxyl groups on alpha, beta, or gamma carbon atoms). The carboxylic acid may be a mono-, di-, or tri-carboxylic acid. In general, the organic acid may contain from about one to about twenty-two carbon atoms. Suitable organic acids, by way of non-limiting example, include acetic acid, adipic acid, alpha hydroxy methionine, alpha hydroxy cysteine, benzoic acid, butyric acid, citric acid, formic acid, fumaric acid, glutaric acid, glycolic acid, lactic acid, malic acid, mandelic acid, oxalic acid, propionic acid, sorbic acid, succinic acid, tartaric acid, uric acid, or salt thereof any of the foregoing. In specific embodiments, the feed additive comprises alpha hydroxy methionine or salt thereof and at least one additional organic acid chosen from benzoic acid, butyric acid, citric acid, fumaric acid, or lactic acid. The salt of alpha hydroxyl methionine may be calcium, copper, iron, manganese, zinc, or combination thereof.

The amount of organic acids present in the feed additive can and will vary depending upon the identity of the acids. In general, the total amount of organic acids in the feed additive may be at least about 50%, at least about 60%, at least about 70%, at least about 75%, at least about 80%, or at least about 85%.

In specific embodiments, the feed additive may comprise or consist of alpha hydroxy methionine (or 2-hydroxy-4-(methylthio)butanoic acid) or salt thereof, benzoic acid, and fumaric acid. The salt of alpha hydroxy methionine may be a calcium salt.

In certain embodiments, the amount of alpha hydroxy methionine or salt thereof may range from about 30% to about 45% by weight, the amount of benzoic acid may range from about 15% to about 25% by weight, the amount of fumaric acid may range from about 35% to about 50% by weight, provided that the total amount is no more than 100% by weight. In other embodiments, the amount of alpha hydroxy methionine or salt thereof may range from about 33% to about 40% by weight, the amount of benzoic acid may range from about 18% to about 22% by weight, the amount of fumaric acid may range from about 38% to about 46% by weight, provided that the total amount is no more than 100% by weight. In some embodiments, the amount of alpha hydroxy methionine or salt thereof may range from about 36% to about 37% by weight, the amount of benzoic acid may range from about 19% to about 21% by weight, the amount of fumaric acid may range from about 41% to about 43% by weight, provided that the total amount is no more than 100% by weight. In some embodiments, the weight ratio of alpha hydroxy methionine or salt thereof to benzoic acid to fumaric acid may range from about 1:0.5-0.6:1.1-1.2.

The amount of feed additive administered to the animal may range depending upon the identity of organic acids present in the feed additive. In some embodiments, the amount of feed additive administered may range from about 0.05% to about 1% by weight of the feed provided to the animal. In certain embodiments, the amount of feed additive administered may be about 0.1%, about 0.15%, about 0.2%, about 0.3%, about 0.4%, about 0.5%, about 0.6% or about 0.7% by weight of the feed provided to the animal. In specific embodiments, the amount of feed additive administered may be about 0.5% by weight of the feed provided to the animal.

In some embodiments, the feed additive may comprise at least one excipient. Suitable excipients include antioxidants, fillers, binders, or combinations thereof.

In specific embodiments, the optional excipient may be an antioxidant. The antioxidant may be natural or synthetics. Non-limiting examples of suitable antioxidants include ascorbyl palmitate, ascorbyl stearate, butylated hydroxyanisole (BHA), butylated hydroxytoluene (BHT), 6-ethoxy-1, 2-dihydro-2,2,4-trimethylquinoline (ethoxyquin), ethyl gallate, propyl gallate, tertiary butyl hydroquinone (TBHQ), or combination thereof.

In still other embodiments, the optional excipient may be a filler. Suitable fillers include without limit cellulose, microcrystalline cellulose, cellulose ethers (e.g., ethyl cellulose, methyl cellulose, hydroxypropyl cellulose, hydroxypropyl methylcellulose, sodium carboxymethylcellulose, etc.), cellulose esters (i.e., cellulose acetate, cellulose butyrate, and mixtures thereof), starches (e.g., corn starch, rice starch, potato starch, tapioca starch, and the like), modified starches, pregelatinized starches, phosphated starches, starch-lactose, starch-calcium carbonate, sodium starch glycolate, glucose, fructose, sucrose, lactose, xylose, lactitol, mannitol, malitol, sorbitol, xylitol, maltodextrin, trehalose, calcium carbonate, calcium sulfate, calcium phosphate, calcium silicate, magnesium carbonate, magnesium oxide, clays, talc, or combinations thereof.

In further embodiments, the optional excipient may be a binder. Non-limiting examples of suitable binders include starches (e.g., corn starch, potato starch, wheat starch, rice starch, and the like), pregelatinized starch, hydrolyzed starch, cellulose, microcrystalline cellulose, cellulose derivatives (e.g., methylcellulose, ethylcellulose, hydroxypropylcellulose, hydroxypropylmethylcellulose, sodium carboxymethylcellulose, and the like), saccharides (e.g., sucrose, lactose, and so forth), sugar alcohols (e.g., maltitol, sorbitol, xylitol, polyethylene glycol, and the like), alginates (e.g., alginic acid, alginate, sodium alginate, and so forth), gums (e.g., gum arabic, guar gum, gellan gum, xanthan gum, and the like), pectins, gelatin, C12-C18 fatty acid alcohols, polyvinylpyrrolidinone (also called copovidone), polyethylene oxide, polyethylene glycol, polyvinyl alcohols, waxes (e.g., candelilla wax, carnauba wax, beeswax, and so forth), or combinations of any of the forgoing.

(c) Administration Strategies

The feed additive may be co-administered to the animal together with the feed. In some embodiments, the feed additive may be added to and/or mixed with the prepared animal feed. In other embodiments, the feed additive may be added to and/or mixed with a contaminated feed ingredient prior to blending of feed ingredients to prepare the animal feed.

Alternatively, the feed additive may be administered to the animal separately from the contaminated feed. For example, the feed additive may be administered to the animal at a different time or a different location.

(d) Animals

Suitable animals include, but are not limited to, livestock or agricultural animals, companion animals, zoological animals, and research animals. The animal may range in age from newborn to elderly. In certain embodiments, the animal may be a livestock or agricultural animal. Non-limiting examples of suitable livestock or agricultural animals may include cows, cattle, pigs, goats, sheep, poultry, llamas, alpacas, aquatic animals (e.g., farmed fish and shellfish), and the like. In other embodiments, the animal may be a companion animal. Non-limiting examples of companion animals may include pets such as dogs, cats, horses, rabbits, and birds. In yet other embodiments, the animal may be a zoological animal. As used herein, a "zoological animal" refers to an animal that may be found in a zoo. Such animals may include non-human primates, large cats, wolves, bears, hippos, kangaroos, etc. In still other embodiments, the animal may be a research or laboratory animal. Non-limiting examples of a research of laboratory animal include rodents (e.g., mice, rats, guinea pigs, hamsters, etc.), canines, felines, and non-human primates. In specific embodiments, the animal may be an agricultural animal, e.g., the animal may be a pig. The pig may be a piglet, a weaner pig, a grower pig, a feeder pig, a finisher pig, a breeder pig, a farrowing pig, and so forth.

(e) Outcomes of the Method

In general, administration of the feed additive to animals exposed to viral contaminated feeds may result in reduced viral loads or reduced amounts of viral nucleic acids as compared to animals that consumed viral contaminated feed but were not administered the feed additive. In some embodiments, the animals administered the feed additive may not display clinical symptoms of infection. In still other embodiments, the animals administered the feed additive may have increased weight gain, increased average daily gain (AGD), and/or increased feed conversion ratio (FCR).

(II) Methods for Reducing Risk of Viral Infection in Animals

Another aspect of the present disclosure encompasses methods for reducing the risk of viral infection in animals whose feed may or may not be virus contaminated. In particular, the methods comprise administering to the animal an effective concentration of a feed additive, wherein the feed additive comprises a mixture of organic acids, and wherein the viral status of the animal's feed is unknown (i.e., it may be contaminated or it may not be contaminated). In other words, the method may be preventive, precautionary, or prophylactic.

The animal's feed may be contaminated with any of the viruses listed above in section (I)(a). The feed additive is as detailed above in section (I)(b). Various strategies for administering the feed additive are described above in section (I)(c). Suitable animal and outcomes are detailed above in sections (I)(d) and (I)(e).

(III) Feed Ingredients or Feeds Comprising the Feed Additive

Still another aspect of the present disclosure encompasses feed ingredients or feeds comprising the feed additive, as detailed above in section (I)(b).

(a) Feed Ingredients

Non-limiting examples of feed ingredients vitamins, minerals, amino acids or amino acid analogs, antioxidants, polyunsaturated fatty acids, enzymes, prebiotics, probiotics, postbiotics, herbs, pigments, approved antibiotics, or combinations thereof.

In some embodiments, the feed ingredient may be one or more vitamins. Suitable vitamins include vitamin A, vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid), vitamin B12, vitamin C, vitamin D, vitamin E, vitamin K, other B-complex vitamins (e.g., choline, carnitine, adenine), or combinations thereof. The form of the vitamin may include salts of the vitamin, derivatives of the vitamin, compounds having the same or similar activity of a vitamin, and metabolites of a vitamin.

In further embodiments, the feed ingredient may be one or more amino acids. Non-limiting suitable amino acids include standard amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), non-standard amino acids (e.g., L-DOPA, GABA, 2-aminobutyric acid, and the like), amino acid analogs (e.g., alpha hydroxy analogs), or combinations thereof.

In alternate embodiments, the feed ingredient may be one or more antioxidants. Suitable antioxidants include, but are not limited to, ascorbic acid and its salts, ascorbyl palmitate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline (ethoxyquin), ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivatives thereof, vitamin Q10, wheat germ oil, zeaxanthin, or combinations thereof.

In still other embodiments, the feed ingredient may be one or more polyunsaturated fatty acids. Suitable polyunsaturated fatty acids (PUFAs) include long chain fatty acids with at least 18 carbon atoms and at least two carbon-carbon double bonds, generally in the cis-configuration. In specific embodiments, the PUFA may be an omega fatty acid. The PUFA may be an omega-3 fatty acid in which the first double bond occurs in the third carbon-carbon bond from the methyl end of the carbon chain (i.e., opposite the carboxyl acid group). Suitable examples of omega-3 fatty acids include all-cis 7,10,13-hexadecatrienoic acid; all-cis-9,12, 15-octadecatrienoic acid (alpha-linolenic acid, ALA); all-cis-6,9,12,15,-octadecatetraenoic acid (stearidonic acid); all-cis-8,11,14,17-eicosatetraenoic acid (eicosatetraenoic acid); all-cis-5,8,11,14,17-eicosapentaenoic acid (eicosapentaenoic acid, EPA); all-cis-7,10,13,16,19-docosapentaenoic acid (clupanodonic acid, DPA); all-cis-4,7,10,13,16,19-docosahexaenoic acid (docosahexaenoic acid, DHA); all-cis-4,7,10,13,16,19-docosahexaenoic acid; and all-cis-6,9, 12,15,18,21-tetracosenoic acid (nisinic acid). In an alternative embodiment, the PUFA may be an omega-6 fatty acid in which the first double bond occurs in the sixth carbon-carbon bond from the methyl end of the carbon chain. Examples of omega-6 fatty acids include all-cis-9,12-octadecadienoic acid (linoleic acid); all-cis-6,9,12-octadecatrienoic acid (gamma-linolenic acid, GLA); all-cis-11,14-eicosadienoic acid (eicosadienoic acid); all-cis-8,11,14-eicosatrienoic acid (dihomo-gamma-linolenic acid, DGLA); all-cis-5,8,11,14-eicosatetraenoic acid (arachidonic acid, AA); all-cis-13,16-docosadienoic acid (docosadienoic acid); all-cis-7,10,13,16-docosatetraenoic acid (adrenic acid); and all-cis-4,7,10,13,16-docosapentaenoic acid (docosapentaenoic acid). In yet another alternative embodiment, the PUFA may be an omega-9 fatty acid in which the first double bond occurs in the ninth carbon-carbon bond from the methyl end of the carbon chain, or a conjugated fatty acid, in which at least one pair of double bonds are separated by only one single bond. Suitable examples of omega-9 fatty acids include cis-9-octadecenoic acid (oleic acid); cis-11-eicosenoic acid (eicosenoic acid); all-cis-5,8,11-eicosatrienoic acid (mead acid); cis-13-docosenoic acid (erucic acid), and cis-15-tetracosenoic acid (nervonic acid). Examples of conjugated fatty acids include 9Z,11E-octadeca-9,11-dienoic acid (rumenic acid); 10E,12Z-octadeca-9,11-dienoic acid; 8E,10E,12Z-octadecatrienoic acid (α-calendic acid); 8E,10E,12E-octadecatrienoic acid (β-Calendic acid); 8E,10Z,12E-octadecatrienoic acid (jacaric acid); 9E,11E,13Z-octadeca-9,11,13-trienoic acid (α-eleostearic acid); 9E,11E,13E-octadeca-9,11,13-trienoic acid (β-eleostearic acid); 9Z,11Z,13E-octadeca-9,11,13-trienoic acid (catalpic acid), and 9E,11Z,13E-octadeca-9,11,13-trienoic acid (punicic acid).

In still other embodiments, the feed ingredient may be one or more probiotics, prebiotics, or postbiotics. Probiotics, prebiotics, and postbiotics include agents derived from yeast or bacteria that promote good digestive health. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In an exemplary embodiment, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae.* Probiotics, prebiotics, and postbiotics may also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Lactobacillus acidophilus, Lactobacillus casei, Enterococcus faecium, Bifidobacterium bifidium, Propionibacterium acidipropionici, Propionibacteriium freudenreichii,* and *Bifidobacterium pseudolongum.*

In alternate embodiments, the feed ingredient may be one or more enzymes or enzyme variants. Suitable non-limiting examples of enzymes include amylases, carbohydrases, cellulases, esterases, galactonases, galactosidases, glucanases, hemicellulases, hydrolases, lipases, oxidoreductases, pectinases, peptidases, phosphatases, phospholipases, phytases, proteases, transferases, xylanases, or combinations thereof.

In further embodiments, the feed ingredient may be one or more herbals. Suitable herbals and herbal derivatives, as used herein, refer to herbal extracts, and substances derived from plants and plant parts, such as leaves, flowers, and roots, without limitation. Non-limiting exemplary herbals and herbal derivatives include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, capsicum, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. John's wort, sarsaparilla, sassafras, saw palmetto, scullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, *yucca*, or combinations thereof.

In still other embodiments, the feed ingredient may be one or more natural pigments. Suitable pigments include, without limit, actinioerythrin, alizarin, alloxanthin, β-apo-2'-carotenal, apo-2-lycopenal, apo-6'-lycopenal, astacein, astaxanthin, azafrinaldehyde, aacterioruberin, aixin, α-carotine, β-carotine, γ-carotine, β-carotenone, canthaxanthin, capsanthin, capsorubin, citranaxanthin, citroxanthin, crocetin, crocetinsemialdehyde, crocin, crustaxanthin, cryptocapsin, α-cryptoxanthin, β-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-α-carotenone, semi-β-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, α-zeacarotene, or combinations thereof.

In yet other embodiments, the feed ingredient may be one or more antibiotics approved for use in livestock and poultry (i.e., antibiotics not considered critical or important for human health). Non-limiting examples of approved antibiotics include bacitracin, carbadox, ceftiofur, enrofloxacin, florfenicol, laidlomycin, linomycin, oxytetracycline, roxarsone, tilmicosin, tylosin, and virginiamycin.

In further embodiments, the feed ingredient may be a protein meal (e.g., soybean meal, corn meal, corn gluten meal, corn germ meal, fish meal, blood meal, bone meal, poultry by-product meal, etc.), protein cakes (e.g., soybean cake, soybean oil cake, and so forth), grains (e.g., corn grain, oat grain, wheat grain, milled grains, brewer's grains, sprouted brains, and so forth), pelleted feeds, oils or fats (e.g., vegetable oils, oilseed oils, rendered animal fats, and so forth).

(b) Feeds

Animal feeds are designed to satisfy an animal's maintenance energy requirements by providing protein, carbohydrate, and/or fat to the animal. Examples of such ingredients include grains, forage products, feed meals, feed concentrates, and the like.

Suitable grains include corn, soybeans, wheat, barley, oats, sorghum, rye, rice, and other grains, and grain meals (e.g., soybean meal).

Forage products are feed ingredients such as vegetative plants in either a fresh (pasture grass or vegetation), dried, or ensiled state and may incidentally include minor proportions of grain (e.g., kernels of corn that remain in harvested corn plant material after harvest). Forage includes plants that have been harvested and optionally fermented prior to being provided to ruminants as a part of their diet. Thus, forage includes hay, haylage, and silage. Examples of hay include harvested grass, either indigenous to the location of the ruminants being fed or shipped to the feeding location from a remote location. Non-limiting examples of hay include alfalfa, Bermuda grass, bahia grass, limpo grass, rye grass, wheat grass, fescue, clover, and the like as well as other grass varieties that may be native to the location of the ruminants being provided the ruminant feed ration.

It is beneficial if the forage is relatively high quality (i.e., contains relatively levels of metabolizable nutrients which permit the animal to satisfy its nutrient and maintenance energy requirements before reaching its consumption capacity). If the forage is of low quality, the animal may not metabolize it adequately to achieve desired performance effects (e.g., satisfy its nutrient and/or maintenance energy requirements), not only compromising the nutritional benefit from the forage per se, but also causing the animal to feel full or bloated, and possibly deterring it from consuming sufficient nutrients.

Haylage is a forage product that has been naturally fermented by harvesting a hay crop while the sap is still in the plant. The harvested hay or hay bales are then stored in an air-tight manner in which fermentation can occur. The fermentation process converts the sugars in the plants into acids which lower the pH of the harvested hay and preserves the forage.

Silage, similar to haylage, is a forage product that is produced from the harvest, storage and fermentation of green forage crops such as corn and grain sorghum plants. These crops are chopped, stems and all, before the grain is ready for harvest. The plant material is stored in silos, storage bags, bunkers, or covered piles causing the material to ferment, thereby lowering the pH and preserving the plant material until it can be fed.

Forage products also include high fiber sources and scrap vegetation products such as green chop, corncobs, plant stalks, and the like.

Feed concentrates are feedstuffs that are high in energy and low in crude fiber. Concentrates also include a source of one or more ingredients that are used to enhance the nutritional adequacy of a feed supplement mix, such as vitamins and minerals.

The feed may be supplemented with a fat source. Non-limiting fats include plant oils, fish oils, animal fats, yellow grease, fish meal, oilseeds, distillers' grains, or combinations thereof. The fat source will generally comprise from about 1% to about 10% of the dry mass of the total feed ration, more preferably from about 2% to about 6%, and most preferably from about 3% to about 4%.

Feeds typically are formulated to meet the nutrient and energy demands of a particular animal. The nutrient and energy content of many common animal feed ingredients have been measured and are available to the public. The National Research Council has published books that contain tables of common ruminant feed ingredients and their respective measured nutrient and energy content. Additionally, estimates of nutrient and maintenance energy requirements are provided for growing and finishing cattle according to the weight of the cattle. National Academies of Sciences, Engineering, and Medicine. 2016. Nutrient Requirements of Beef Cattle: Eighth Revised Edition. Washington, D.C.: The National Academies Press, pp. 396-403, which is incorporated herein in its entirety. This information can be utilized by one skilled in the art to estimate the nutritional and maintenance energy requirements of animal and determine the nutrient and energy content of animal feed ingredients.

EXAMPLES

The following examples illustrate various embodiments of the present disclosure.

Example 1: Evaluation of the Efficacy of Feed Additive at Reducing Infection Following Consumption of Viral Contaminated Feed The objective of this study was to evaluate the efficacy of a feed additive comprising a blend of 2-hydroxy-4-(methylthio)butanoate (HMTBA) calcium analog, benzoic acid, and fumaric acid (ACTIVATE® DA, Novus International) at reducing the risk of infection following consumption of feed contaminated with PRRSV 174, PEDV and SVA.

Materials and Methods.

The study was conducted in the Pipestone Applied Research Biosafety level 2 research facility (Pipestone, Minn.). The experimental design consisted of 3 groups, including:

Group 1: complete feed mixed with Feed Additive at a 0.5% inclusion rate,

Group 2: complete feed mixed with Feed Additive at a 0.15% inclusion rate, and

Group 3: complete feed positive control (no Feed Additive).

The study was based on the hypothesis that differences in the infection events will differ across groups, and utilized a 15-day period with room as the experimental unit with 100 pigs/room (12 pens/room) and a designated feed bin/room.

Pigs (15 kg) originated from a source herd documented to be free of all 3 viral pathogens by monthly testing and clinical history. Viral challenge involved a 454 g "Ice Block Model", consisting of 100 mL SVA (5 logs TCID50/mL, Ct=20.72), 100 mL PRRSV 174 (5 logs TCID50/mL, Ct=21.38), 100 mL PEDV (5 logs TCID50/mL, Ct=24.25) and balanced with 154 mL minimal essential media (MEM). Blocks were frozen at −80° C. and dropped into each feed bin on days 0 and 6 of the study. The blocks proceeded to melt, with liquid permeating the feed, which was then augured into room for pigs to consume via natural feeding behavior.

Ante-mortem samples, including oral fluids and Swiffer samples of feeders, were collected across the 12 pens from each of the 3 rooms at 0 and 6 days post-inoculation (DPI) of feed. Feed samples alone were collected at 14 DPI. For collection of feed samples, individual Swiffer cloths were drawn across the feed trough, contacting feed particles present. Cloths were immersed in sterile saline and a 3 mL aliquot was decanted for testing. Post-mortem samples were collected from 30 pigs from each room at 14 DPI. Samples collected included tonsil for SVA, serum for PRRSV and rectal swabs for PEDV. Samples were evaluated for the presence of viral nucleic acid by PCR and nucleic acid sequencing of the ORF 5 was performed on select samples, as needed. In addition, start and end weights were collected from all pigs (0 and 14 DPI). Differences in Ct value (cycle threshold) between groups were analyzed for significance ($p<0.05$) using ANOVA or T test.

Results.

Pigs were scored daily for the presence of the following clinical signs: lameness/vesicles (SVA), dyspnea/weight loss/rough hair coat (PRRSV); and diarrhea (PEDV). Throughout the course of the study period, none of the aforementioned clinical signs were noted in the treated rooms. In contrast, by days 10-14 clinical signs of lameness (2 of 12 pens), dyspnea (6 of 12 pens), rough hair coat (5 of 12 pens) and diarrhea (8 of 12 pens) were noted in the positive control room.

All samples collected at 0 DPI were negative for all 3 viruses as determined by PCR. Results of virus detection in feed samples and in oral fluid samples at 6 DPI are summarized in tables 1 and 2, while results from 14 DPI feed samples are summarized in table 3. Post-mortem results are summarized in table 4, while growth performance is summarized in table 5. Differences found to be significant ($p<0.05$) between groups are bolded in the tables.

TABLE 1

Detection of viral RNA in feed samples collected on 6 DPI

| | Feed Additive | | | |
|---|---|---|---|---|
| Virus | 0.5% Inclusion | 0.15% Inclusion | Control | p value |
| SVA | 2/12 Samples Mean Ct = 37.8$^a$ | 2/12 Samples Mean Ct = 36.5$^a$ | 6/12 Samples Mean Ct = 32.9$^b$ | 0.03 |
| PRRSV | 0/12 Samples[1] | 8/12 Samples[1] Mean Ct = 35.6$^a$ | 6/12 Samples[1,2] Mean Ct = 33.7$^a$ | 0.30 |
| PEDV | 0/12 Samples | 11/12 Samples Mean Ct = 34.2$^a$ | 4/12 Samples Mean Ct = 33.6$^a$ | 0.68 |

$^{a,b}$Different superscripts within the same row are different ($p < 0.05$)
[1]PRRS vaccine strain 142 sequenced
[2]PRRS challenge strain 174 sequenced

TABLE 2

Detection of viral RNA in oral fluids collected on 6 DPI

| | Feed Additive | | | |
|---|---|---|---|---|
| Virus | 0.5% Inclusion | 0.15% Inclusion | Control | p value |
| SVA | 4/12 Samples Mean Ct = 35.6$^a$ | 6/12 Samples Mean Ct = 35.8$^a$ | 7/12 Samples Mean Ct = 31.4$^b$ | 0.097 |
| PRRSV | 7/12 Samples[1] Mean Ct = 35$^a$ | 12/12 Samples[1] Mean Ct = 29.5$^b$ | 12/12 Samples[1,2] Mean Ct = 31.1$^b$ | 0.01 |
| PEDV | 0/12 Samples | 12/12 Samples Mean Ct = 31.6$^a$ | 3/12 Samples Mean Ct = 32.8$^a$ | 0.66 |

$^{a,b}$Different superscripts within the same row are different ($p < 0.05$)
[1]PRRS vaccine strain 142 sequenced
[2]PRRS challenge strain 174 sequenced

TABLE 3

Detection of viral RNA in feed samples collected on 14 DPI

| | Feed Additive | | | |
|---|---|---|---|---|
| Virus | 0.5% Inclusion | 0.15% Inclusion | Control | p value |
| SVA | 0/12 Samples | 0/12 Samples | 0/12 Samples | N/A |
| PRRSV | 0/12 Samples | 0/12 Samples | 0/12 Samples | N/A |
| PEDV | 12/12 Samples Mean Ct = 34.8$^a$ | 12/12 Samples Mean Ct = 32.2$^b$ | 12/12 Samples Mean Ct = 32.8$^b$ | 0.01 |

$^{a,b}$Different superscripts within the same row are different ($p < 0.05$),
NA = not applicable

TABLE 4

Postmortem measures of virus exposure at day 14

| | Feed Additive | | | |
|---|---|---|---|---|
| Virus | 0.5% Inclusion | 0.15% Inclusion | Control | p value |
| SVA | 0/30 Samples | 0/30 Samples | 2/30 Samples | N/A |
| PRRSV | 0/6 Samples | 0/6 Samples | 2/6 Samples 174 sequenced | N/A |
| PEDV | 7/30 Samples Mean Ct = 35.4$^a$ | 28/30 Samples Mean Ct = 30.9$^b$ | 28/30 Samples Mean Ct = 31.6$^b$ | 0.01 |

$^{a,b}$Different superscripts within the same row are different ($p < 0.05$),
NA = not applicable

TABLE 5

Descriptive statistics of pig bodyweights (lbs)

| | Feed Additive | | | |
|---|---|---|---|---|
| | 0.5% Inclusion | 0.15% Inclusion | Control | P value |
| Day 0 Mean | 28.3 | 28.4 | 28.6 | 0.96 |
| SD | 1.6 | 1.3 | 2.6 | |
| SEM | 0.46 | 0.38 | 0.76 | |
| CV | 0.057 | 0.046 | 0.092 | |
| Day 14 Mean | 58.0$^a$ | 53.8$^b$ | 54.5$^b$ | 0.01 |
| SD | 2.2 | 2.8 | 3.6 | |
| SEM | 0.61 | 0.82 | 1.06 | |
| CV | 0.033 | 0.052 | 0.067 | |

$^{a,b}$Different superscripts within the same row are different

Discussion.

Across both levels of Feed Additive in the feed, no clinical signs of PRRS, SVA, or PEDv were detected. Post-mortem, there were no signs of PRRS or SVA in the Feed Additive groups. However, PEDv infection occurred in both Feed Additive groups at significantly different levels. In contrast, evidence of PEDV, SVA and PRRSV 174 infection and clinical signs were observed in the positive control population. In addition, a significant difference in growth was observed in pigs fed the Feed Additive at a 0.5% inclusion rate as compared to a 0.15% inclusion rate and the positive controls.

Under the conditions of the study, the following conclusions were drawn. 1) Feed in the bins was successfully contaminated using the ice block, resulting in delivery of all 3 viruses to all rooms. 2) Transmission of PRRSV, PEDV and SVA via the feed was documented in the positive control group. 3) These data support the risk of contaminated feed as a means of viral entry to farms. 4) Neither level of Feed Additive "sterilized" the feed. 5) Pigs fed label or reduced dose of Feed Additive remained free of PRRSV 174 and SVA. 6) Pigs fed label or reduced dose of Feed Additive became infected with PEDV, but significant differences in percent positive and Ct values were detected across groups. 7) Clinical signs were not detected in either Feed Additive room. 8) Pigs fed the label dose of Feed Additive grew faster than those fed the reduced dose.

What is claimed is:

1. A method for reducing risk of infection due to consumption of feed contaminated with a virus, the method comprising administering to an animal in need thereof an effective concentration of a feed additive, wherein the feed additive comprises a mixture of organic acids, and the virus is porcine epidemic diarrhea virus (PEDV), porcine reproductive and respiratory syndrome virus (PRRSV), or Seneca Valley A virus (SVA), wherein the additive is administered at a level of about 0.05% to about 1% by weight of the feed.

2. The method of claim 1, wherein the mixture of organic acids comprises two or more organic acids chosen from acetic acid, adipic acid, 2 hydroxy-4-methylthio-butanoic acid, alpha hydroxy cysteine, benzoic acid, butyric acid, citric acid, formic acid, fumaric acid, glutaric acid, glycolic acid, lactic acid, malic acid, mandelic acid, oxalic acid, propionic acid, sorbic acid, succinic acid, tartaric acid, uric acid, or salt of any of the foregoing.

3. The method of claim 2, wherein the mixture of organic acids comprises or consists of 2 hydroxy-4-methylthio-butanoic acid or salt thereof, benzoic acid, and fumaric acid.

4. The method of claim 3, wherein the mixture of organic acids comprises from about 30% to about 45% by weight of 2-hydroxy-4-methylthio-butanoic acid or salt thereof, about 15% to about 25% by weight of benzoic acid, about 35% to about 50% by weight of fumaric acid, provided that the total amount is no more than 100% by weight.

5. The method of claim 1, wherein the feed additive is co-administered with the feed contaminated with the virus.

6. The method of claim 1, wherein the feed additive is administered, spatially or temporally, separately from the feed contaminated with the virus.

7. The method of claim 1, wherein the feed additive is administered at a level of 0.05% by weight of the feed.

8. The method of claim 1, wherein the animal is a pig.

9. The method of claim 1, wherein the animal has a reduced viral load as compared to an animal fed the contaminated feed but not administered the feed additive.

10. The method of claim 1, wherein the animal has an increased average weight gain as compared to an animal fed the contaminated feed but not administered the feed additive.

* * * * *